United States Patent [19]

Bowers

[11] 4,014,901

[45] Mar. 29, 1977

[54] SYNTHETIC HORMONES FOR INSECT CONTROL

[75] Inventor: William S. Bowers, Bowie, Md.

[73] Assignee: The United States of America as represented by the Secretary of Agriculture, Washington, D.C.

[22] Filed: July 2, 1975

[21] Appl. No.: 592,697

Related U.S. Application Data

[62] Division of Ser. No. 363,294, May 23, 1973, which is a division of Ser. No. 78,577, Oct. 6, 1970, abandoned.

[52] U.S. Cl. .................. 260/340.9; 260/348 R; 260/484 R; 260/593 R; 260/603 R; 260/614 A; 260/617 R; 260/632 R; 260/654 R; 424/278; 424/311

[51] Int. Cl.$^2$ ...................................... C07D 317/10

[58] Field of Search .......................... 260/340.9 R

[56] References Cited

UNITED STATES PATENTS

| | | | |
|---|---|---|---|
| 2,578,861 | 12/1951 | Thomas et al. | 260/340.9 X |
| 3,346,643 | 10/1967 | Reed, Jr. et al. | 260/340.9 X |

*Primary Examiner*—Ethel G. Love
*Attorney, Agent, or Firm*—M. Howard Silverstein; William E. Scott; David G. McConnell

[57] ABSTRACT

Ethers of open chain terpenoid compounds and their monoepoxides were synthesized and found to mimic the juvenile hormones of insects and to be extremely effective as insect control agents.

1 Claim, No Drawings

SYNTHETIC HORMONES FOR INSECT CONTROL

This is a division of application, Ser. No. 363,294, dated May 23, 1973, which in turn is a division of application, Ser. No. 78,577, filed Oct. 6, 1970, now abandoned.

A non-exclusive, irrevocable, royalty-free license in the invention herein described throughout the world for all purposes of the United States Government, with the power to grant sublicenses for such purposes, is hereby granted to the Government of the United States of America.

This invention relates to insect control and more particularly to compounds and to the preparation of compounds that have high juvenile hormone activity and which are highly ovicidal to insect eggs.

There is considerable concern throughout the world about the persistence of many insecticides and insecticide residues in our environment and the potential hazard that these materials represent to human populations. In addition, many species of insect pests have become resistant or immune to many of the insecticides on the market. Thus, more selective chemicals are required which will not pose a threat to human populations and to which the insects will not develop resistance.

The compounds of the present invention should be suitable replacements for the insecticides now being used to control stored product insects and many social pests such as fireants and termites. In addition, it may be feasible to use these compounds in field applications to control a wide variety of insects, the toxicity of the compounds to vertebrates should be insignificant, and the cost to produce them commercially should be very competitive with that of well known insecticides.

One object of this invention is to provide a means for achieving selective, safe, economical control of insect pests.

Another object is to provide chemical compounds that prevent insect maturation when applied topically, when fed to insects or when applied in a vapor state as a fumigant, to an insect in an immature stage of growth.

A further object of this invention is to provide compounds that adversely affect the biological function of insects, particularly their ability to mature to an adult stage.

In general, according to the present invention the terpenoid ethers and their corresponding epoxides are synthesized and found to prevent insect maturation when applied to immature stages of several species of insects by topical application, by feeding or by fumigation (exposure to vapor). Thus an immature insect exposed to these compounds is unable to metamorphose into a normal adult. Topical application of as little as 10.0 nanograms (0.01 μg) of the more active compounds in this series is sufficient to prevent metamorphosis. The insect which emerges from the treated pupa retains immature genitalia which preclude copulation and reproduction. The insects die shortly after molting to this adultoid condition. Also, when used as a vapor or as a dip treatment for eggs the compounds drastically reduce egg hatch.

The compounds of this invention having the following general formula.

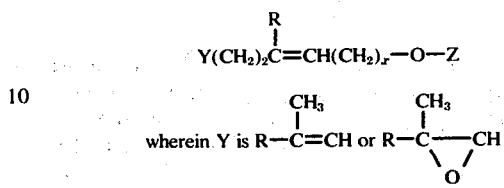

R is straight chain alkyl containing from 1—2 carbon atoms such as $CH_3$—, $CH_3CH_2$—,
x is a number from 1 to 2, and
Z is one of the following groups:

—$CH_2CH_2$—$O(CH_2)_nCH_3$ in which n is 0–3 ;

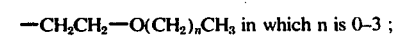

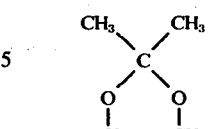

—$CH_2$—$CH$——$CH_2$; —$CH_2COO(CH_2)_nCH_3$ in which n is 0–1;

—$CH_2CH$——$CH_2$; and —$CHO$—$(CH_2)_nCH_3$ in which n is 0–3.

The terpenoid portions of the compounds were prepared in part by the Marc Julia synthesis [Bull. Soc. Chem. France 1072, (1960)] as outlined below.

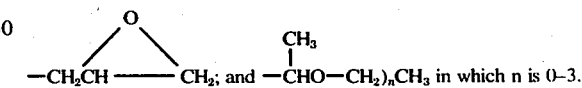

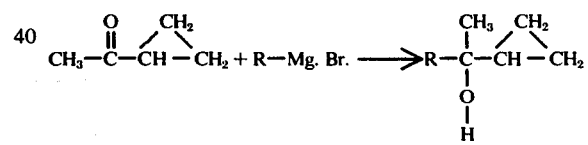

Oxidation was performed with chromic acid solution in acetone [J. Chem. Soc. 2548(1953)]

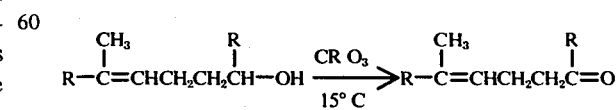

The vinyl alcohols are prepared by the grignard reaction with vinyl magnesium bromide (or chloride) in tetrahydrofuran.

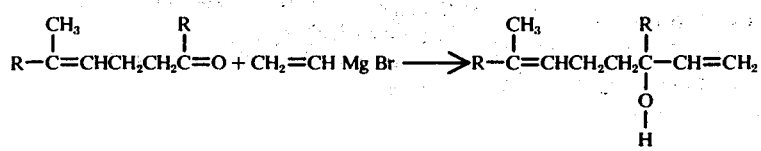

The vinyl alcohols were converted to the allylic bromides by treatment with hydrogen bromide in aqueous or acetic acid solution. Thus, an aliquot of the vinyl alcohol was added dropwise to a rapidly stirred ice cold aqueous or acetic acid solution containing 2 molar equivalents of hydrogen bromide. When addition was complete, stirring was continued for 20 minutes and then the reaction mixture was poured into an excess of ice cold 5% sodium carbonate solution, extracted with diethyl ether and washed to neutrality with water. After drying the ethereal extracts over sodium sulfate and removal of the solvent in vacuo, the allylic bromide were obtained in nearly quantitative yield.

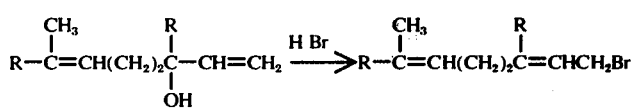

Another series of compounds in which the terpenoid carbon chain was one carbon longer were prepared in a similar manner except that the bromides were prepared by a continuation of the Julia synthesis as follows:

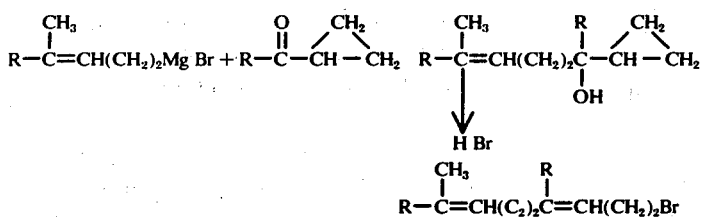

Compounds of the general formula $$Y(CH_2)_2\overset{R}{\underset{|}{C}}=CH(CH_2)_x-O-A$$

wherein Y is $R-\overset{CH_3}{\underset{|}{C}}=CH$ or 

R is a straight chain alkyl containing from 1 to 2 carbon atoms such as $CH_3-$, $CH_3CH_2-$;
x is a number from 1 to 2; and
A is $-CH_2CH_2-O(CH_2)_n CH_3$ in which n is 0 to 3;
were synthesized by coupling the foregoing bromides with the respective alcohols of A to form the corresponding ethers by refluxing the bromides or stirring at room temperature for several hours with a slight molar excess of the alcohols and a base such as powdered potassium hydroxide or potassium teritary butoxide in an anhydrous solvent such as diethyl ether, dimethoxyethane or dimethyl formamide. Alternatively, the reactants were sealed in a small reaction bomb and place in an oven at 150° C for 2–4 hours.

The reaction mixture was then diluted with water and extracted several times with hexane. The hexane extracts were combined and washed to neutrality with water. The hexane portion was dried over sodium sulfate and the solvent removed in vacuo to yield the crude ethers.

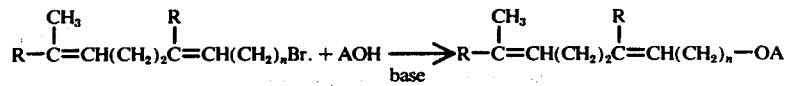

The crude ethers obtained from the foregoing reactions were purified by chromatography over florisil. The crude material was put on a florisil column (30 gm florisil/gm crude material) in hexane and eluted stepwise with increasing concentrations of diethyl ether in hexane. Purity was determined by gas-liquid chromatography and infra-red spectroscopy to be greater than 99%.

Compounds of the general formula

-continued

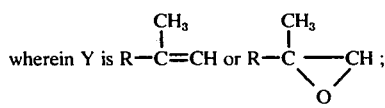

R is a straight chain alkyl containing from 1–2 carbon atoms such as $CH_3-$, $CH_3CH_2-$;
$x$ is a number from 1 to 2; and
E is — $CH_2COO(CH_2)_nCH$ or
in which $n$ is 0 to 1 were presented from the terpenoid alcohols.

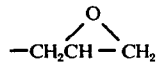

The allylic terpenoid alcohols were prepared from their corresponding vinyl analogs by chromic acid oxidation [J. Chem. Soc. 2548 (1953)] to the conjugated aldehyde, followed by reduction to the primary alcohol with a metal hydride such as sodium borohydride in methanol, or lithium aluminum hydride in ether.

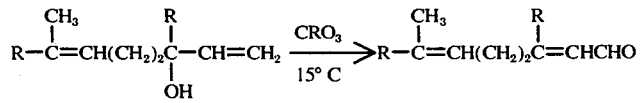

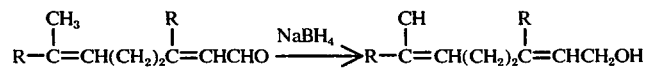

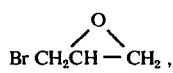

The primary halides of E, (Br $CH_2COO(CH_2)_n CH_3$, or were coupled with the terpenoid alcohols under basis conditions in a reaction bomb, under reflux, or by stirring at room temperature for an extended period of time.

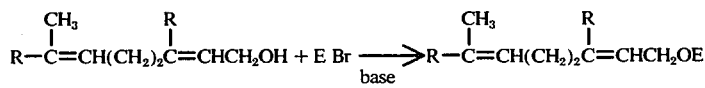

The crude ethers were purified by chromatography over florisil as previously described. Purity was determined by gas-liquid chromatography and infra-red spectroscopy to be greater than 99%. Compounds of the general structure

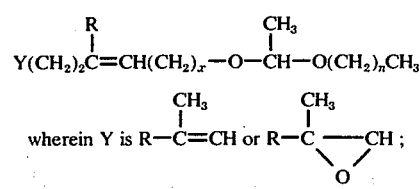

R=Straight chain alkly containing from 1–2 carbon atoms such as $CH_3-$, $CH_3CH_2-$;
$x$ is a number from 1 to 2; and
$n$ is a number from 0 to 3
were prepared by stirring the terpenoid alcohols for 2 hours at room temperature with the appropriate vinyl ether in the presence of a catalytic amount of hydrochloric acid.

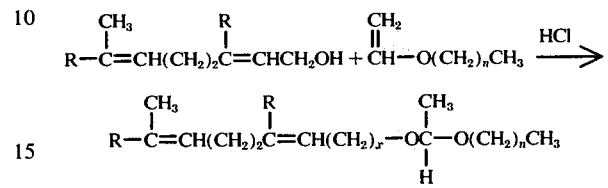

The reaction was complete in 1 hour and the reaction mixture was extracted with diethyl ether and washed successively with 5% aqueous sodium carbonate and water. The ethereal extract was dried over anhydrous sodium sulfate. The crude product was isolated by evaporation of the solvent in vacuo.

The desired compounds were purified by column chromatography over florisil as previously described. Purity was determined by gas-lipid chromatography and infra-red spectroscopy to be greater than 99%.

All of the ethers prepared by the following syntheses were then epoxidized by stirring them in an organic solvent such as benzene, chloroform or methylene chloride during the addition of a slight molar excess of an epoxidizing agent such as m-chloro perbenzoic acid.

Epoxidation occurred selectively at the terminal double bond within a few minutes to one hour. The reaction mixture was washed with 5% sodium carbonate and then with water to neutrality, and dried over sodium sulfate. Solvent was removed in vacuo.

The epoxides were purified by chromatography over florisil as previously described.

Purity was ascertained by gas-liquid chromatography and infrared spectroscopy to be greater than 99%.

The compounds and their epoxides prepared by the above procedures are shown in Table I.

Although the general procedures just described are undoubtedly adequate for those skilled in the art, the following examples further illustrate the preparation of compounds within the scope of each of the general structures shown above.

Synthesis of Compound 49 in Table I

-continued

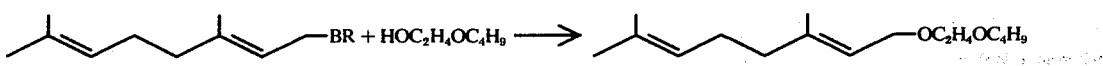

In a 500 ml. boiling flask, 10.8 g. ethylene glycol butyl ether, was combined with 10.2 g. potassium tert-butoxide and 10 g. geranyl bromide in 100 ml. dimethoxyethane. The reaction mixture was stirred at room temperature for 16 hrs. and then poured into 200 ml. of hexane and washed 2X with water and 1X with saturated aqueous sodium chloride solution. The organic layer was dried anhydrous sodium sulfate and the hexane removed in vacuo. 13.6 g. of crude compound was recovered and found to be suitable for the subsequent epoxidation.

Epoxidation of Compound 49 in Table I

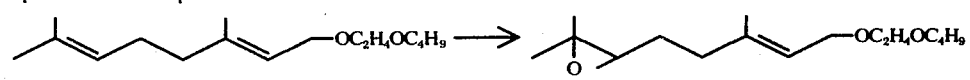

Dissolved 4 g. of the Compound 49 in 50 ml. CH$_2$Cl$_2$ and with stirring added 3.2 g. m-chloroperbenzoic acid in aliquots. Stirred 30 min. and then made the solution basic with 10% aqueous sodium carbonate. Stripped off the solvent in vacuo. Residue was dissolved in diethyl ether and wased in a separatory funnel with 10% sodium carbonate 2X, and water 2X. Dried organic layer over anhydrous sodium sulfate. Stripped off solvent in vacuo. Crude epoxide yield was 3.8 gm. Fractionation of the crude expoxide over 60 gm. of florisil by stepwise elution with increasing concentrations of diethyl ether in hexane gave 3.0 g. pure epoxide. (Compound No. 57)

Synthesis of Compound 65 in Table II

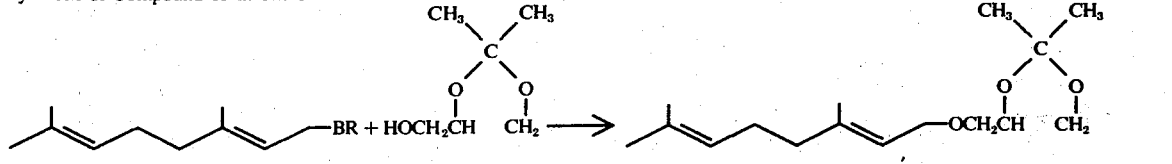

Combined 10 gm. glycerol acetonide and 5.4 gm. potassium tertbutoxide in 50 ml. dimethoxyethane and stirred for 20 min. Added 8.2 g. geranyl bromide and continued stirring at room temperature for 16 hrs. Filtered, stripped off dimethoxyethane, dissolved residue in diethyl ether and washed with water in a separatory funnel 3X. Dried organic layer over anhydrous sodium sulfate and stripped off solvent in ether. Crude ether Compound 65 yield was 6.7 gm. 3 gm. of Compound 65 was fractionated by column chromatography over 70 gm. of florisil. Stepwise elution with increasing concentrations of diethyl ether in hexane gave 1.9 g. of pure Compound 65.

Epoxidation of Compound 65 in Table II

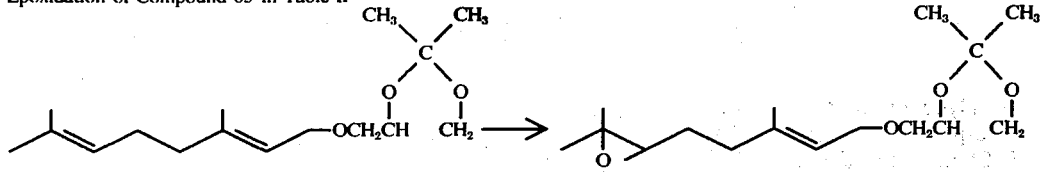

Dissolved 1.3 g. of Compound 65 in 30 ml. CH$_2$Cl$_2$ and added in aliquots 1.0 gm. of m-Chloroperbenzoic acid. Reaction stirred 30 min. Solution made basis with 10% aqueous sodium carbonate. Stripped off solvent in vacuo. Residue dissolved in diethyl ether and washed in a separatory funnel with 10% sodium carbonate 2X and with water 2X. Dried over anhydrous sodium sulfate. Crude epoxide, Compound 73, was 1.3 g. The crude epoxide was fractionated by column chromatography as specified for Compound 65. Yield of pure epoxide, Compound 73, was 950 mg. (Compound 73)

Synthesis of Compound 81 in Table I

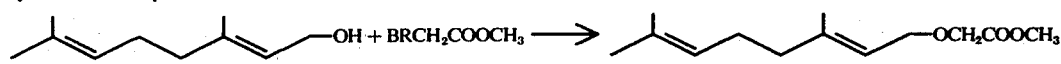

Stirred 5 gm geraniol with 3.5 gm. potassium tert-butoxide in 50 ml. dimethoxyethane for 30 minutes. Added to above 5.8 g. of methyl bromacetate and stirred at room temperature for 16 hrs. Reaction mixture dissolved in 200 ml. diethyl ether and washed in a separatory funnel with water 3X. Organic layer dried over anhydrous sodium sulfate. Stripped off solvent in vacuo. Yield of crude Compound 81 was 7.3 gm. The crude ether was chromatographed on a column containing 150 gm. of florisil. Elution with increasing concentrations of diethyl ether in hexane gave a pure fraction containing 1.4 gm. of Compound 81.

Epoxidation of Compound 89 in Table I

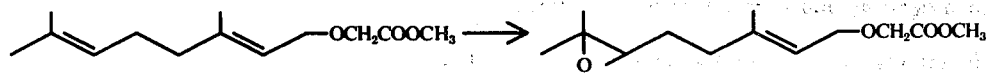

Dissolved 1 gm. of Compound 81 in 25 ml. of CHCl₃—Hexane (3–2) containing 0.4 gm. sodium bicarbonate with stirring in an ice bath. To this was added dropwise 1.0 gm. m-chloroperbenzoic acid in 25 ml. of CHCl₃-Hexane (3–2). After addition, stirring in the ice bath was maintained for 15 min. Sodium sulfite was added to destroy any excess peracid. The reaction mixture was dissolved in about 200 ml. of diethyl ether and washed in a separatory funnel with 10% aqueous sodium carbonate 2X and water 2X. Organic layer was dried over anhydrous sodium sulfate and the solvent stripped off in vacuo. Yield of crude Compound 89 was 1.26 gm. The crude Compound 89 was fractionated over 30 gm. of florisil as specified for Compound 81 and 770 mg. of pure Compound 89 was obtained. Analysis by gas-chromatography and infrared. (Compound 89)

Organic layer dried over anhydrous sodium sulfate. Yield of crude Compound 121 was 2.0 gm. Column chromatography of Compound 121 over 60 gm. florisil by stepwise elution with increasing concentrations of diethyl ether in hexane gave 713 mg. of pure Compound 121. Analysis by gas-chromatography and infrared. (Compound 121)

Synthesis of Compound 145 in Table I

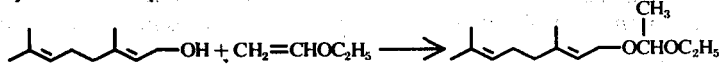

Geraniol (10 gm.) in 25 ml. diethyl ether was added dropwise to 14 g. ethyl vinyl ether containing 1 drop of concentrated HCl. After addition, stirring was maintained for 2 hrs. in a warm water bath (ca. 50° C.). The reaction mixture was dissolved in 200 ml. of diethyl ether and washed in a separatory funnel with 5% aqueous sodium carbonate 1X, and water 3X. The organic layer was dried over anhydrous sodium sulfate. The solvent was stripped off in vacuo. The crude acetal yield was 14.5 gm. Filtration of 5 gm. of the acetal in hexane through a column containing 150 gm. of florisil gave a quantitative return of 5 gm. of pure acetal Compound 145. Purity ascertained by gas-chromatography and infrared analysis.

Synthesis of Compound 113 in Table I

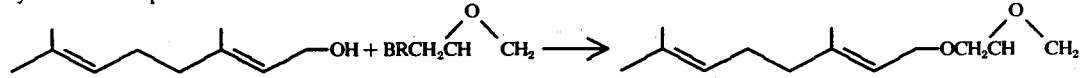

Dissolved 5 g. geraniol in 50 ml. dimethoxyethane containing 3.5 g potassium tert-butoxide with stirring for 30 min. Added 4.4 g. epibromohydrin and stirred at room temperature for 3 hrs. Filtered, dissolved in about 250 ml. diethyl ether and washed with water 3X in a separatory funnel. The organic layer was dried over anhydrous sodium sulfate and the solvent stripped off in vacuo. Yield of crude either was 7.6 gm. The crude ether was fractionated by column chromatography over 150 gm. of florisil. Stepwise elution with increasing concentrations of ether in hexane gave 2.24 gm. of pure Compound 113.

Epoxidation of Compound 145 in Table I

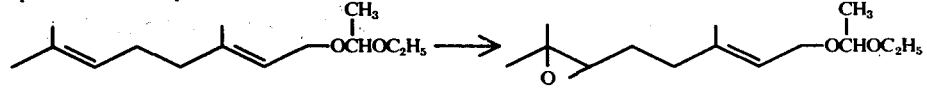

To a stirred solution of 5 gm. of Compound 145 in 100 ml. hexane was added dropwise 4.94 gm. m-chloroperbenzoic acid dissolved in 100 ml. CH₂Cl₂. After addition, stirring was continued for 20 min. Excess peracid was destroyed with sodium sulfite. The reaction mixture was made basic with 5% aqueous potassium hydroxide and the solvent stripped off in vacuo. The residue was dissolved in diethyl ether and washed in a Epoxidation of Compound 113 in Table I

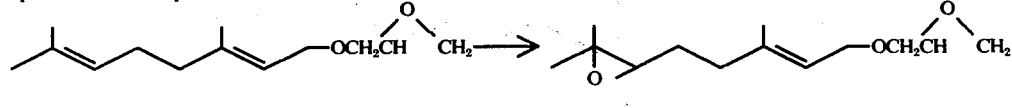

Dissolved 2.24 g. of Compound 113 in 50 ml. CH₂Cl₂ and with stirring added 2.2 g. m-chloroperbenzoic acid in aliquots. Stirred an additional 30 min., made basic with 10% aqueous sodium carbonate, dissolved in 200 ml. diethyl ether and washed with 10% aqueous sodium carbonate 2X and with water 2X in a separatory funnel.

separatory funnel with 5% aqueous potassium hydroxide 1X and with water 3X. Organic layer was dried over anhydrous sodium sulfate and the solvent stripped off in vacuo. Yield of crude Compound 153 was 5.0 gm. Fractionization of 5.0 gm. of Compound 153 by column chromatography over 100 gm. of florisil by stepwise elution with increasing concentrations of diethyl ether in hexane gave 3.0 gm. of pure Compound 153. Analysis by gas-chromatography and infrared. (Compound 153).

The morphogenetic effects of some of the compounds in the Tenebrio genitalia assay (Life Sciences 4, 2323-31, 1965) are shown in Table II.

Topical application to Tenebrio pupae of as little as 10 nanograms (0.01 μg) of several compounds (i.e 25, 26, 28, 57, 73) resulted in the retention of complete pupal genitalia after the ultimate molt toward the adult beetle. Topical application of 100 nanograms (0.1 μg) resulted in the development of pupal-adult intermediates.

Topical application of somewhat greater amounts of compounds 76, 89, 121, 153, were required to induce retention of pupal genitalia and/or produce pupal-adult intermediates in Tenebrio. In all cases the affected insects were unable to form normal adults and died during or shortly after their ultimate molt without significant feeding and without any reproduction.

Table III shows the effects of compounds 25, 26, 28, 57, 73, 81, 89, 153, on the Mexican bean beetle. Topical application of nanogram to microgram quantities of these compounds prevents normal adult development and the insects die during the ultimate molt. Topical treatment of Mexican bean beetle eggs with extremely dilute acetone solutions of these compounds caused severe reduction in egg hatch.

Table IV shows the morphogenetic effects of compounds 25, 26, 28, 57, 73, 89, 121, 153, on Tenebrio after exposure of the pupae to the vapors of these compounds. These results exemplify the potential use of the compounds as fumigants.

TABLE I

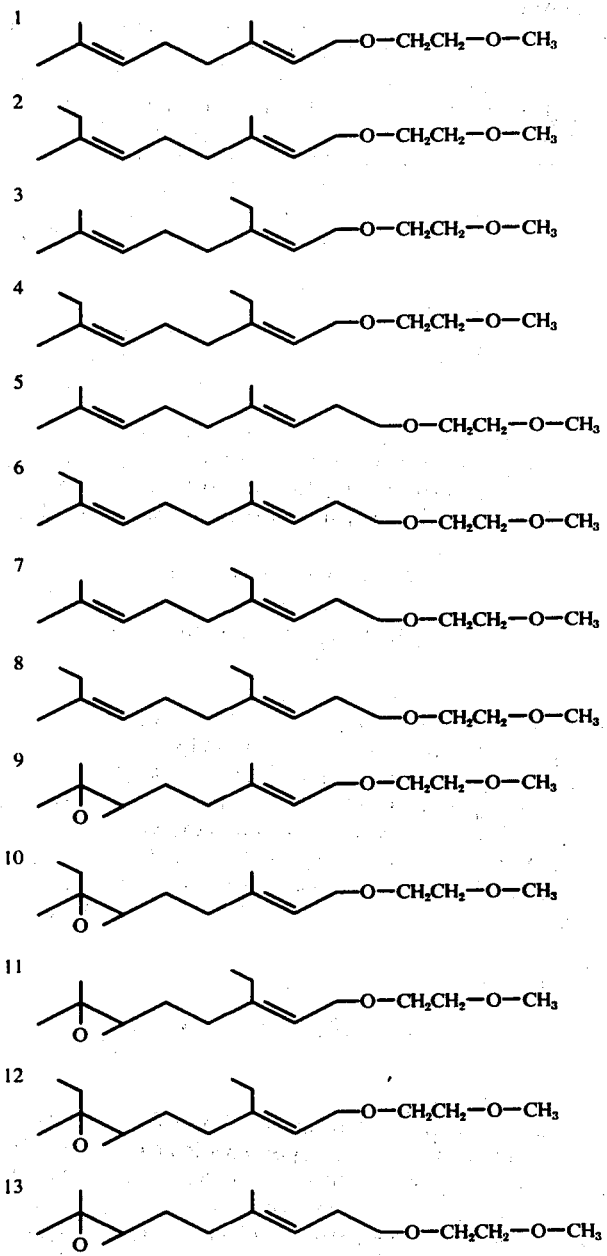

TABLE I-continued
Synthesized Terpenoid Ethers and Their Epoxides
14 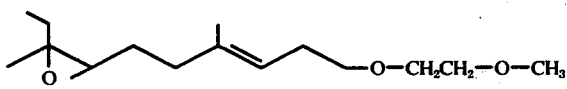
15 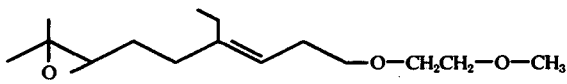
16 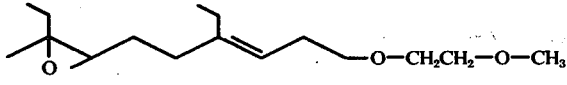
17 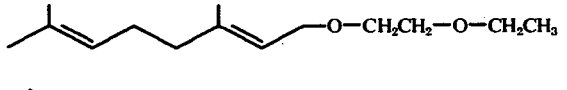
18 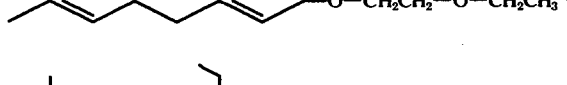
19 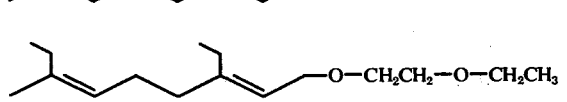
20 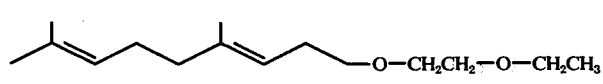
21 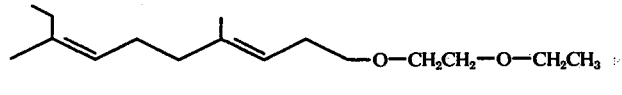
22 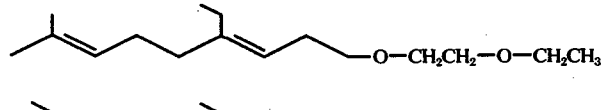
23 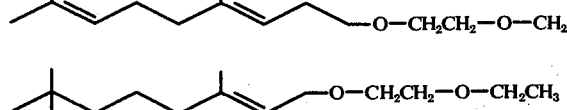
24 
25 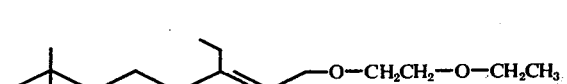
26 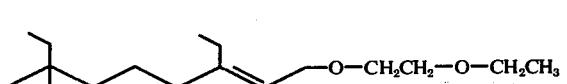
27 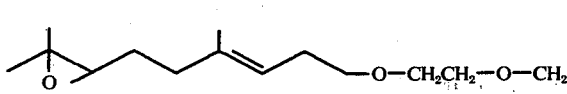
28 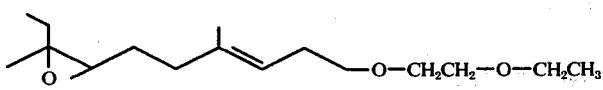
29 
30 

TABLE I-continued
Synthesized Terpenoid Ethers and Their Epoxides
31 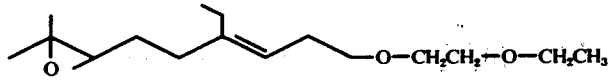
32 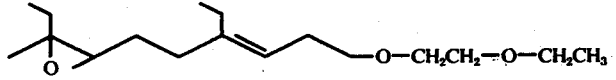
33 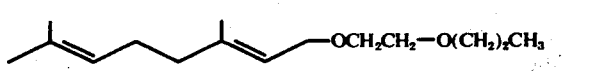
34 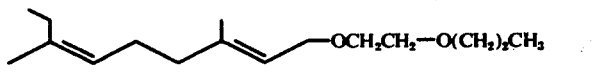
35 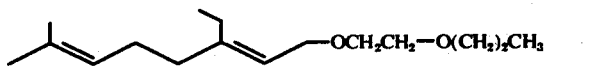
36 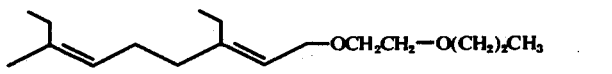
37 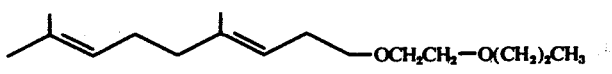
38 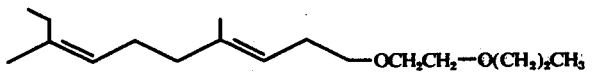
39 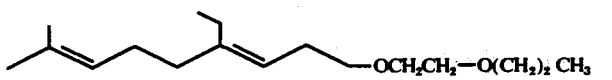
40 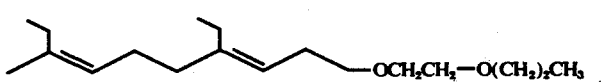
41 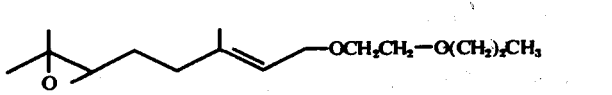
42 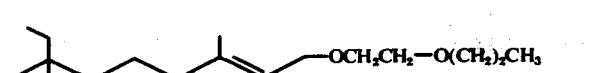
43 
44 
45 
46 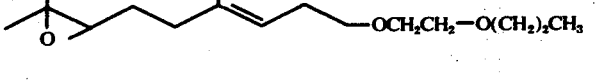
47 

TABLE I-continued
Synthesized Terpenoid Ethers and Their Epoxides
| | |
|---|---|
| 48 | 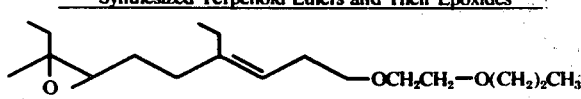 |
| 49 | 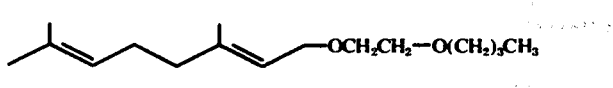 |
| 50 | 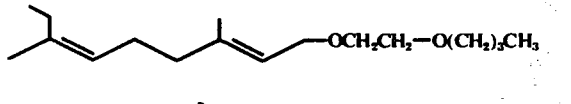 |
| 51 | 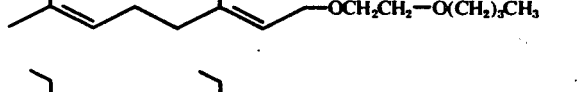 |
| 52 | 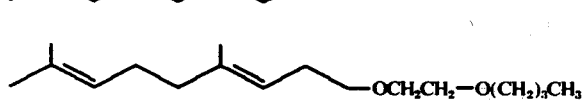 |
| 53 | 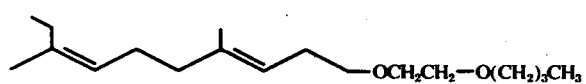 |
| 54 | 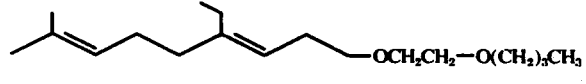 |
| 55 | 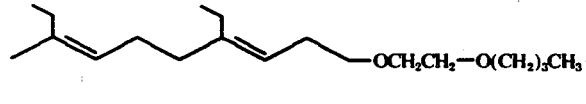 |
| 56 | 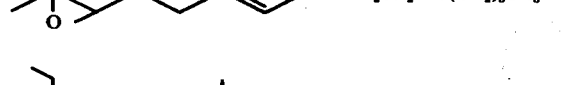 |
| 57 |  |
| 58 |  |
| 59 | 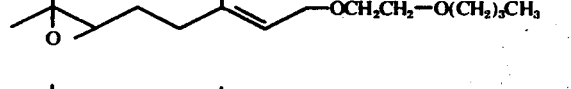 |
| 60 | 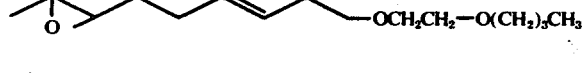 |
| 61 | 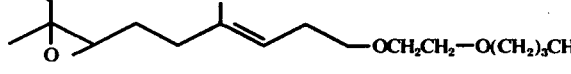 |
| 62 | 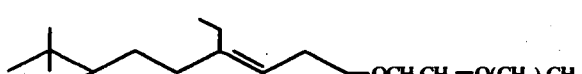 |
| 63 |  |
| 64 | 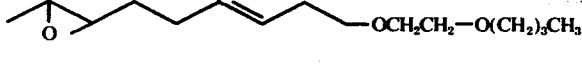 |

TABLE I-continued
Synthesized Terpenoid Ethers and Their Epoxides

65–74: Structural diagrams of terpenoid ether epoxides (not reproducible as text).

TABLE I-continued
Synthesized Terpenoid Ethers and Their Epoxides

| # | Structure |
|---|---|
| 75 | Epoxy-terpenoid with —OCH₂CH—CH₂ linked to acetonide (C(CH₃)₂ bridging two O) |
| 76 | Epoxy-terpenoid with —OCH₂CH—CH₂ acetonide group |
| 77 | Epoxy-terpenoid with —OCH₂CH—CH₂ acetonide group |
| 78 | Epoxy-terpenoid with —OCH₂CH—CH₂ acetonide group |
| 79 | Epoxy-terpenoid with —OCH₂CH—CH₂ acetonide group |
| 80 | Epoxy-terpenoid with —OCH₂CH—CH₂ acetonide group |
| 81 | Terpenoid —OCH₂C(=O)—OCH₃ |
| 82 | Terpenoid —OCH₂C(=O)—OCH₃ |
| 83 | Terpenoid —OCH₂C(=O)—OCH₃ |
| 84 | Terpenoid —OCH₂C(=O)—OCH₃ |
| 85 | Terpenoid —OCH₂C(=O)—OCH₃ |
| 86 | Terpenoid —OCH₂C(=O)—OCH₃ |
| 87 | Terpenoid —OCH₂C(=O)—OCH₃ |
| 88 | Terpenoid —OCH₂C(=O)—OCH₃ |

TABLE I-continued
Synthesized Terpenoid Ethers and Their Epoxides
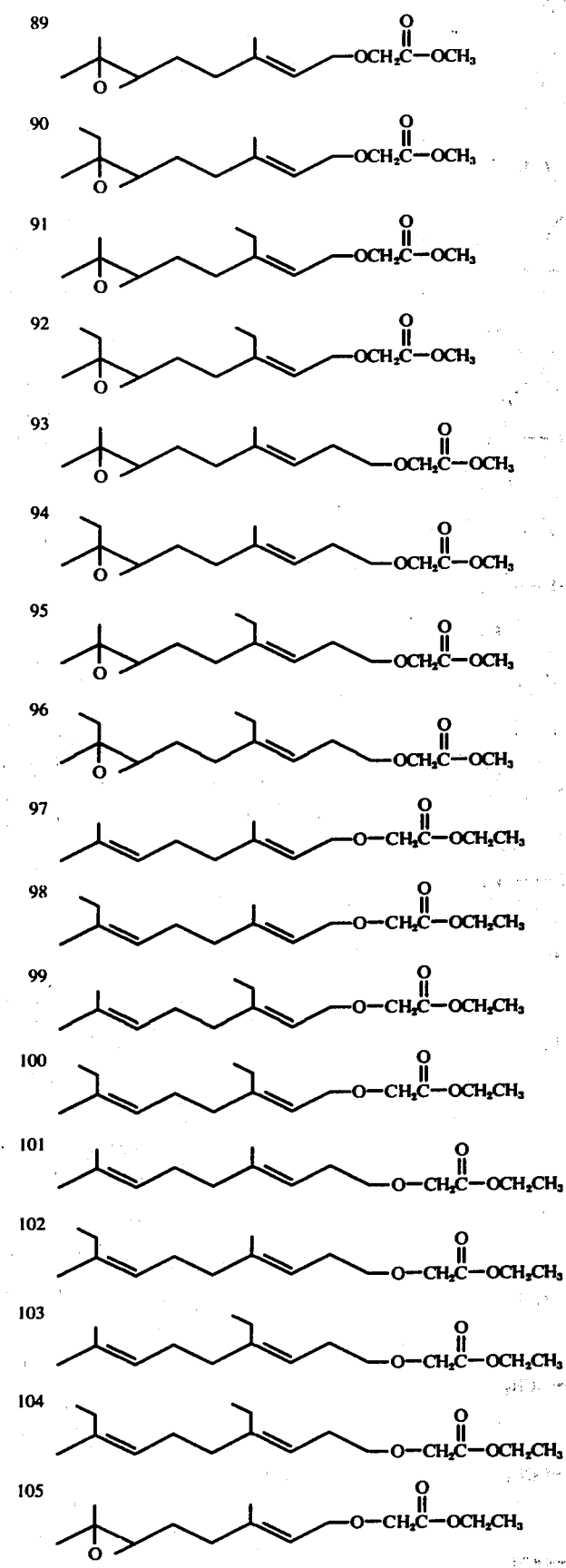

TABLE I-continued

Synthesized Terpenoid Ethers and Their Epoxides

| No. | Structure |
|---|---|
| 106 | epoxide-CH₂CH₂CH=C(CH₃)-CH₂-O-CH₂C(=O)-OCH₂CH₃ |
| 107 | epoxide-CH₂CH₂CH=C(CH₃)-CH₂-O-CH₂C(=O)-OCH₂CH₃ |
| 108 | epoxide-CH₂CH₂CH=C(CH₃)-CH₂-O-CH₂C(=O)-OCH₂CH₃ |
| 109 | epoxide-CH₂CH₂C(CH₃)=CH-CH₂-O-CH₂C(=O)-OCH₂CH₃ |
| 110 | epoxide-CH₂CH₂C(CH₃)=CH-CH₂-O-CH₂C(=O)-OCH₂CH₃ |
| 111 | epoxide-CH₂CH₂C(CH₃)=CH-CH₂-O-CH₂C(=O)-OCH₂CH₃ |
| 112 | epoxide-CH₂CH₂C(CH₃)=CH-CH₂-O-CH₂C(=O)-OCH₂CH₃ |
| 113 | (CH₃)₂C=CH-CH₂CH₂-C(CH₃)=CH-CH₂-O-CH₂CH(–O–)CH₂ |
| 114 | (CH₃)₂C=CH-CH₂CH₂-C(CH₃)=CH-CH₂-O-CH₂CH(–O–)CH₂ |
| 115 | (CH₃)₂C=CH-CH₂CH₂-C(CH₃)=CH-CH₂-O-CH₂CH(–O–)CH₂ |
| 116 | (CH₃)₂C=CH-CH₂CH₂-C(CH₃)=CH-CH₂-O-CH₂CH(–O–)CH₂ |
| 117 | (CH₃)₂C=CH-CH₂CH₂-C(CH₃)=CH-CH₂-O-CH₂CH(–O–)CH₂ |
| 118 | (CH₃)₂C=CH-CH₂CH₂-C(CH₃)=CH-CH₂-O-CH₂CH(–O–)CH₂ |
| 119 | (CH₃)₂C=CH-CH₂CH₂-C(CH₃)=CH-CH₂-O-CH₂CH(–O–)CH₂ |
| 120 | (CH₃)₂C=CH-CH₂CH₂-C(CH₃)=CH-CH₂-O-CH₂CH(–O–)CH₂ |
| 121 | epoxide-CH₂CH₂CH=C(CH₃)-CH₂-O-CH₂CH(–O–)CH₂ |
| 122 | epoxide-CH₂CH₂CH=C(CH₃)-CH₂-O-CH₂CH(–O–)CH₂ |

TABLE I-continued
Synthesized Terpenoid Ethers and Their Epoxides
123 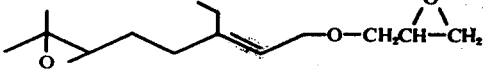
124 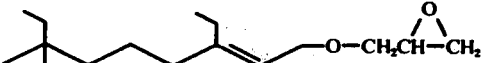
125 
126 
127 
128 
129 
130 
131 
132 
133 
134 
135 
136 
137 
138 
139 

TABLE I-continued
Synthesized Terpenoid Ethers and Their Epoxides
140 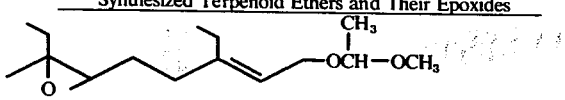
141 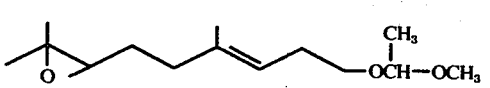
142 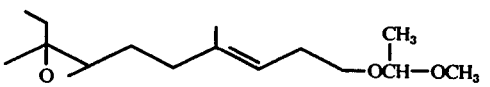
143 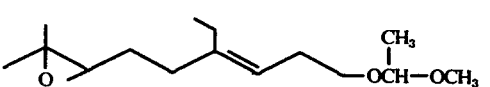
144 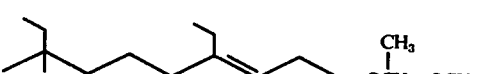
145 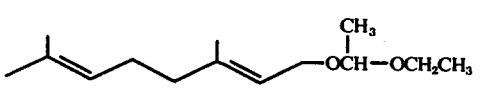
146 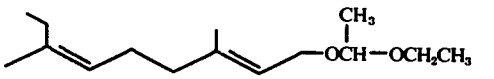
147 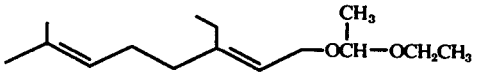
148 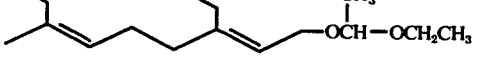
149 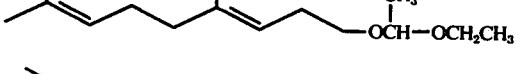
150 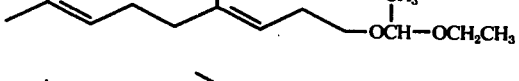
151 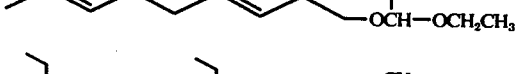
152 
153 
154 
155 
156 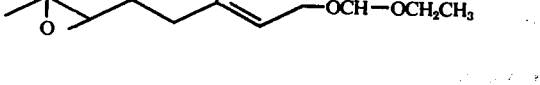

TABLE I-continued
Synthesized Terpenoid Ethers and Their Epoxides

157. Epoxide-CH₂CH₂-CH=C(CH₃)-CH₂-OCH(CH₃)-OCH₂CH₃

158. Epoxide-CH₂CH₂-CH=C(CH₃)-CH₂-OCH(CH₃)-OCH₂CH₃

159. Epoxide-CH₂CH₂-CH=C(CH₃)-CH₂-OCH(CH₃)-OCH₂CH₃

160. Epoxide-CH₂CH₂-CH=C(CH₃)-CH₂-OCH(CH₃)-OCH₂CH₃

161. (CH₃)₂C=CH-CH₂CH₂-C(CH₃)=CH-CH₂-OCH(CH₃)-OCH₂CH₂CH₃

162. (CH₃)₂C=CH-CH₂CH₂-C(CH₃)=CH-CH₂-OCH(CH₃)-OCH₂CH₂CH₃

163. (CH₃)₂C=CH-CH₂CH₂-C(CH₃)=CH-CH₂-OCH(CH₃)-OCH₂CH₂CH₃

164. (CH₃)₂C=CH-CH₂CH₂-C(CH₃)=CH-CH₂-OCH(CH₃)-OCH₂CH₂CH₃

165. (CH₃)₂C=CH-CH₂CH₂-C(CH₃)=CH-CH₂-OCH(CH₃)-OCH₂CH₂CH₃

166. (CH₃)₂C=CH-CH₂CH₂-C(CH₃)=CH-CH₂-OCH(CH₃)-OCH₂CH₂CH₃

167. (CH₃)₂C=CH-CH₂CH₂-C(CH₃)=CH-CH₂-OCH(CH₃)-OCH₂CH₂CH₃

168. (CH₃)₂C=CH-CH₂CH₂-C(CH₃)=CH-CH₂-OCH(CH₃)-OCH₂CH₂CH₃

169. Epoxide-CH₂CH₂-CH=C(CH₃)-CH₂-OCH(CH₃)-OCH₂CH₂CH₃

170. Epoxide-CH₂CH₂-CH=C(CH₃)-CH₂-OCH(CH₃)-OCH₂CH₂CH₃

171. Epoxide-CH₂CH₂-CH=C(CH₃)-CH₂-OCH(CH₃)-OCH₂CH₂CH₃

172. Epoxide-CH₂CH₂-CH=C(CH₃)-CH₂-OCH(CH₃)-OCH₂CH₂CH₃

173. Epoxide-CH₂CH₂-CH=C(CH₃)-CH₂-OCH(CH₃)-OCH₂CH₂CH₃

TABLE I-continued
Synthesized Terpenoid Ethers and Their Epoxides

| 174 | |
| 175 | |
| 176 | |

Table II
Morphogenetic Effects of Representative Compounds in the Tenebrio Genitalia Assay

| Compound Number in Table I | Micrograms of Compound Required to Produce the Indicated Morphogenetic Effects | |
|---|---|---|
| | Pupal-Adult Intermediates [1] | Pupal Genitalia [2] |
| 25 | 0.1 | 0.01 |
| 26 | 0.1 | 0.01 |
| 28 | 0.1 | 0.01 |
| 57 | 0.1 | 0.01 |
| 73 | 0.1 | 0.01 |
| 76 | 1.0 | 0.1 |
| 89 | 100.0 | 1.0 |
| 121 | 100.0 | 1.0 |
| 153 | 100.0 | 10.0 |

[1] Pupal adult intermediates represent an intermediate in which the insect molts to a monster with an essentially pupal abdomen and an adultoid head and thorax.
[2] Pupal genitalia refers to the effect in which the insect is nearly adult but retains immature genitalia.
Each of the above morphogentic effects causes the insect to die shortly thereafter.

Table III
Reduction in Adult Emergence and Egg Hatch of Mexican Bean Beetle Epilachna verivestis

| Compound Number in Table I | Micrograms of Compound Required to cause 90% Reduction in adult Emergence [1] | PPM of Compound Required to cause 90% Reduction in Egg Hatch [2] |
|---|---|---|
| 25 | 0.1 | 1.0 |
| 26 | 0.1 | 10.0 |
| 28 | 0.01 | 1.0 |
| 57 | 0.1 | 100.0 |
| 73 | 0.1 | 10.0 |
| 81 | 10.0 | 100.0 |
| 89 | 100.0 | 100.0 |
| 153 | 0.1 | 1.0 |

[1] Topical treatment of 2-day old prepaupae with an acetone [3] solution of compound.
[2] Topical treatment by dipping egg masses in an acetone [3] solution of compound.
[3] An acetone control conducted for each of the above treatments showed that the solvent contributed nothing to the effect of the compounds.

Table IV
Morphogentic Effects of Representative Compounds on Tenebrio pupae by Fumigation.

| Compound Number in Table I | Micrograms of Compound Required to Produce Pupal-Genitalia and Pupal-Adult intermediates by Vapor Exposure [1] |
|---|---|
| 25 | 0.1 – 5.0 |
| 26 | 0.1 – 5.0 |
| 28 | 0.1 – 5.0 |
| 57 | 0.1 – 5.0 |
| 73 | 0.1 – 5.0 |
| 89 | 0.1 – 5.0 |
| 121 | 1.0 – 10.0 |
| 153 | 1.0 – 10.0 |

[1] Compounds were spread over the lid of a 10 mm diameter petri dish in a small volume of acetone and after evaporation of the acetone the lid was placed over the bottom of the petri dish containing newly molted Tenebrio pupae. The pupae were therefor exposed only to the vapors and did not come in contact with the compound directly. The insects were left in the dish until they underwent the final molt toward the adult.

I claim:

1. A compound of the general formula

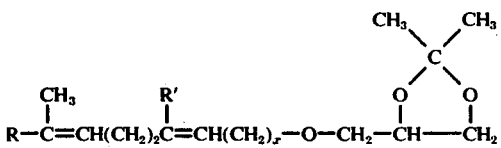

wherein R and R' are selected from the group consisting of methyl and ehtyl; and $x$ is a number from 1 to 2.

* * * * *